US00PP24703P3

(12) United States Plant Patent
Cole, III

(10) Patent No.: US PP24,703 P3
(45) Date of Patent: Jul. 29, 2014

(54) BOXWOOD PLANT NAMED 'LITTLE MISSY'

(50) Latin Name: *Buxus microphylla*
Varietal Denomination: Little Missy

(71) Applicant: CP Delaware, Inc., Wilmington, DE (US)

(72) Inventor: Norman H. Cole, III, Pipestem, WV (US)

(73) Assignee: CP Delaware, Inc., Wilmington, DE (US)

( * ) Notice: Subject to any disclaimer, the term of this patent is extended or adjusted under 35 U.S.C. 154(b) by 53 days.

(21) Appl. No.: 13/573,827

(22) Filed: Oct. 9, 2012

(65) Prior Publication Data

US 2014/0101798 P1 Apr. 10, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Buchanan, Ingersoll & Rooney PC

(57) ABSTRACT

A new and distinct Boxwood plant of unknown parentage is provided that originated as a chance seedling and/or mutation while growing among a block of vegetatively propagated *Buxus microphylla* plants in a plant nursery. The new cultivar readily can be distinguished from other plants of the *Buxus microphylla* species in view of its particularly dense growth habit and smaller dark green foliage. Attractive deep green foliage is formed which well retains its coloration throughout the year in the absence of any substantial color change during the winter. Excellent winter hardiness to at least U.S.D.A. Hardiness Zone No. 5 is displayed. The plant is well suited for providing attractive ornamentation in the landscape throughout the year, even in the coldest months.

2 Drawing Sheets

Botanical/commercial classification: *Buxus microphylla*/ Boxwood Plant.

Varietal denomination: cv. Little Missy.

SUMMARY OF THE INVENTION

The new Boxwood plant of the present invention is a newly found plant that was discovered in a production block of a plant nursery at Pipestem, W. Va., U.S.A., while growing among a block of vegetatively propagated *Buxus microphylla* plants (non-patented in the United States). The parentage of the new plant is unknown; however, it is believed to be of the same species. The plant may be a spontaneous mutation of another plant of the species of unknown causation. It is impossible to further specify the origin of the newly found plant. I was initially attracted to the plant in view of its distinctive appearance primarily attributable to its particularly dense growth habit and its attractive smaller deep green foliage. Had I not discovered and preserved this new plant, it would have been lost to mankind.

The new cultivar has been carefully preserved and has been evaluated to confirm that its characteristics are reliably expressed.

It has been found that the new Boxwood plant of the present invention displays the following combination of characteristics:

(a) forms a dense mounded compact growth habit,
(b) forms attractive deep green foliage throughout the year in the absence of any substantial color change during the winter,
(c) exhibits excellent winter hardiness to at least U.S.D.A. Hardiness Zone No. 5, and (d) is well suited for providing attractive ornamentation in the landscape.

The new evergreen cultivar of the present invention well retains its attractive appearance throughout the year. The foliage is glossy. The deep green coloration of the foliage is well maintained even during the winter, unlike many previously available Boxwood cultivars which tend to assume a brownish-green foliage coloration during the winter. The hardiness of the new cultivar during observations to date has been found to be at least equal to or to exceed most previously known Boxwood cultivars that are known for their superior hardiness. At least five severe winters in the mountains of W. Va., U.S.A., have been well-withstood.

The new cultivar of the present invention can be grown to advantage as attractive ornamentation in the landscape, and is particularly well suited for use to provide low hedges or border plantings or foundation plantings. The new plant takes pruning well and prefers full sun to light shade during observations to date.

The new plant of the present invention can be readily distinguished from other plants of the *Buxus microphylla* species in view of its much smaller leaf size.

Asexual reproduction of the new plant by the use of semi-softwood cuttings has been carried out at West Grove, Pa., U.S.A. during September through November. Such propagation has confirmed that the unique combination of characteristics of the new cultivar has been stably established and is well transmitted to successive generations. The new cultivar asexually reproduces in a true-to-type manner.

The new cultivar has been named 'Little Missy'.

BRIEF DESCRIPTION OF THE PHOTOGRAPHS

The accompanying photographs show as nearly true as it is reasonably possible to make the same in color illustrations of this character, typical specimens of the new variety at an age of approximately eight years when grown outdoors at Pipestem, W. Va., U.S.A.

DETAILED BOTANICAL DESCRIPTION

Figure 1:
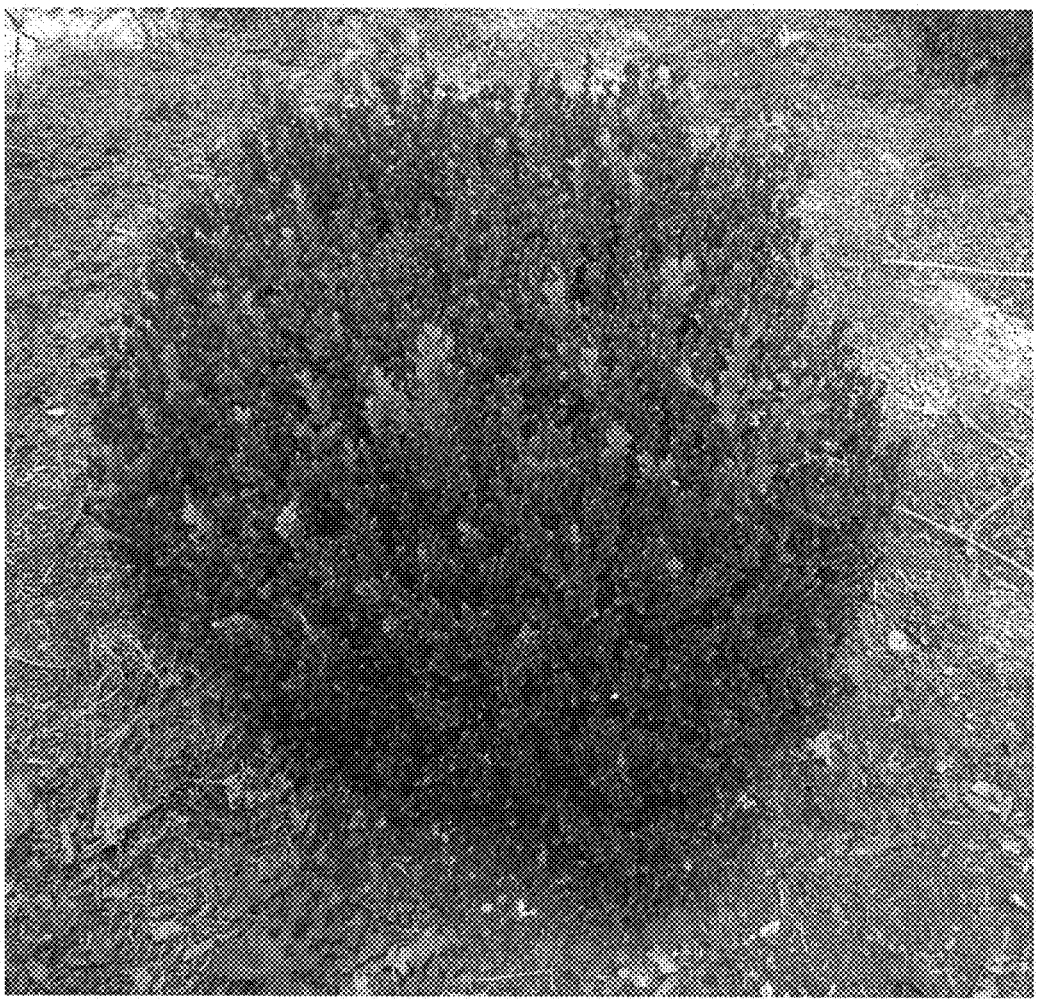
FIG. 1 shows the overall attractive dense mounded compact growth habit.
Figure 2:
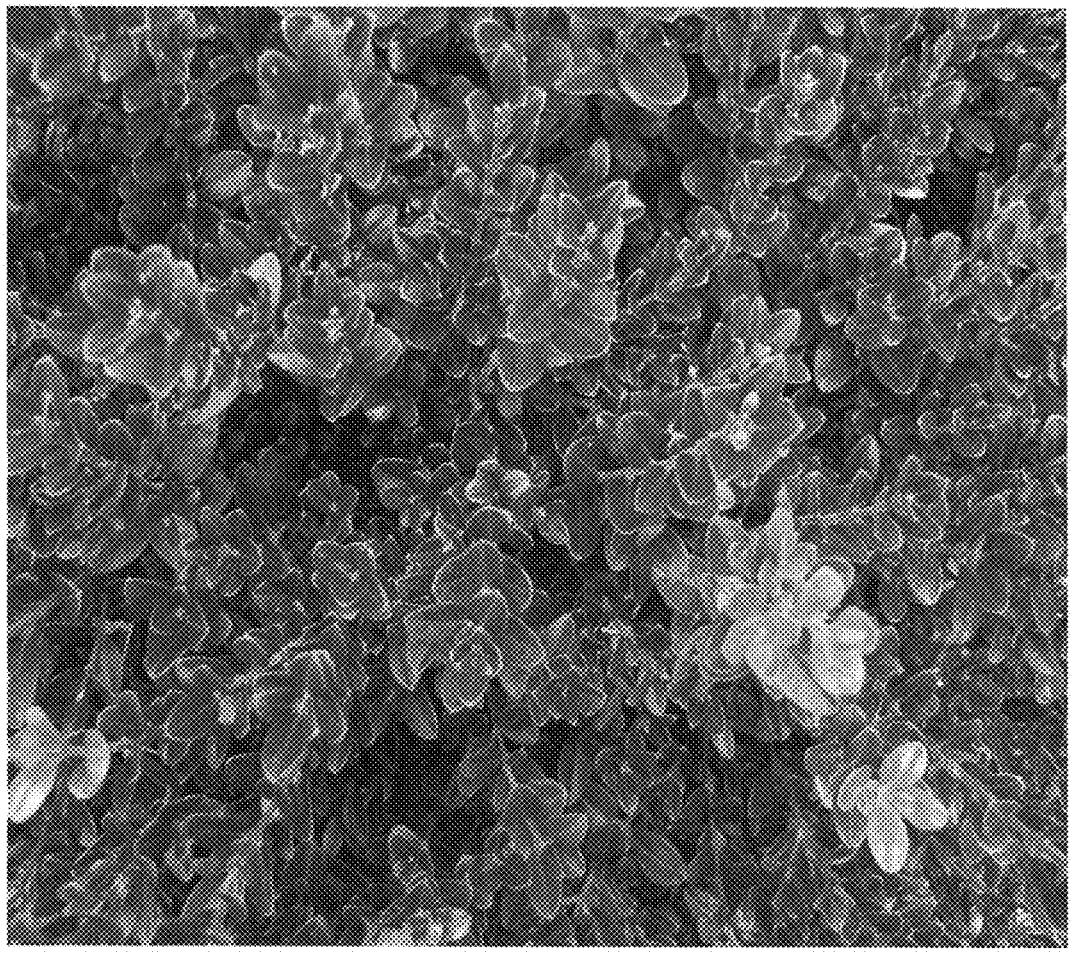
FIG. 2 shows a closer view of the attractive deep green foliage.

The following is a detailed description of the new plant of the present invention which generally was prepared while observing four-year-old plants growing in containers at West Grove, Pa., U.S.A. Color terminology is in accordance with The R.H.S. Colour Chart of The Royal Horticultural Society (1995 Edition or equivalent), London, England, except when general color terms are used which are to be accorded their customary dictionary significance.

Type: Hardy broad-leafed evergreen shrub for garden decoration and general landscape usage.

Botanical classification: *Buxus microphylla.*

Plant:

*Growth habit.*—Fast growing, dense, mounded, and compact.

*Growth rate.*—Commonly the growth rate is approximately 2 to 3 inches per flush.

*Height.*—Approximately 16 inches on average.

*Width.*—Approximately 3½ feet on average.

*Young branches.*—Length: commonly approximately 7.5 cm on average. Diameter: commonly approximately 1 mm on average. Texture: smooth. Color: near Yellow-Green Group 144A.

*Mature branches.*—Length; commonly approximately 17.5 cm on average. Diameter: commonly approximately 3 mm on average. Texture: somewhat rough. Color: Greyed-Orange Group 177B.

*Lateral branches.*—Commonly approximately 5 lateral branches are positioned on a main stem with approximately 225 growing tips. Intermode length: approximately 8 mm on average.

Foliage:

*Juvenile foliage.*—Length: commonly approximately 1.1 cm on average. Width: commonly approximately 0.7 cm on average. Shape: ovate. Base: obtuse. Texture: glossy on upper surface, and smooth on the under surface. Apex: cuspidate. Margin: entire. Color of upper surface: near Yellow-Green Group 144A. Color of under surface: near Yellow-Green Group 144B. Fragrance: somewhat grass-like when crushed.

*Mature foliage.*—Length: commonly approximately 1.6 cm on average. Width: commonly approximately 1 cm on average. Shape: ovate. Apex: generally rounded. Base: obtuse. Texture: glossy on the upper surface, and smooth on the under surface with a pronounced midrib. Margin: entire. Color of upper surface: commonly Green Group 139A. Color of lower surface: commonly Yellow-Green Group 144A. Fragrance: somewhat acrid when crushed.

*Petioles.*—Length: approximately 1 mm on average when mature. Diameter: commonly approximately 1 mm. Texture: smooth. Color: near Yellow-Green Group 144A.

Inflorescence: No flowers, fruit, or seeds are observed to date.

Development:

*Hardiness.*—To at least U.S.D.A. Hardiness Zone No. 5. Grows well in U.S.D.A. Hardiness Zone Nos. 5 to 9.

*Disease resistance.*—No disease problems have been observed during observations to date.

*Insect tolerance.*—No insect damage has been observed during observations to date.

Plants of the new 'Little Missy' variety have not been observed under all possible environmental conditions to date. Accordingly, it is possible that the phenotypic expression may vary somewhat with changes in light intensity and duration, cultural practices, and other environmental conditions.

I claim:

1. A new and distinct Boxwood plant possessing the following characteristics:

(a) forms a dense mounded compact growth habit, (b) forms attractive deep green foliage throughout the year in the absence of any substantial color change during the winter, (c) exhibits excellent winter hardiness to at least U.S.D.A. Hardiness Zone No. 5, and (d) is well suited for providing attractive ornamentation in the landscape;

substantially as illustrated and described.

* * * * *